(12) United States Patent
Lebner et al.

(10) Patent No.: US 7,332,641 B2
(45) Date of Patent: Feb. 19, 2008

(54) INTERLACED COMPOSITIONS AND METHODS OF PRODUCTION

(75) Inventors: Michael Lebner, Wellesley Hills, MA (US); Raymond Barbuto, Dagsboro, DE (US)

(73) Assignee: Clozex Medical LLC, Wellesley Hills, MA (US)

( * ) Notice: Subject to any disclaimer, the term of this patent is extended or adjusted under 35 U.S.C. 154(b) by 845 days.

(21) Appl. No.: 10/683,861

(22) Filed: Oct. 10, 2003

(65) Prior Publication Data

US 2005/0080453 A1  Apr. 14, 2005

(51) Int. Cl.
*A61F 13/00* (2006.01)
(52) U.S. Cl. .......................... 602/42; 602/41; 602/54; 606/213; 606/215; 606/216
(58) Field of Classification Search ........ 606/213–216; 602/41–43, 52, 57, 58
See application file for complete search history.

(56) References Cited

U.S. PATENT DOCUMENTS

| | | |
|---|---|---|
| RE24,906 E | 7/1859 | Goodfellow |
| 1,074,413 A | 9/1913 | De Baun et al. |
| 1,230,444 A | 6/1917 | Teed |
| 1,969,188 A | 8/1934 | Spicer |
| 2,196,296 A | 5/1940 | Flynn |
| 2,532,011 A | 11/1950 | Dahlquist et al. |
| 2,762,371 A | 9/1956 | Guio |
| 2,818,865 A | 6/1958 | Jacoby, Jr. |
| 3,020,186 A | 2/1962 | Lawrence |
| 3,329,548 A | 7/1967 | Blatz |
| 3,389,827 A | 6/1968 | Abere |

(Continued)

FOREIGN PATENT DOCUMENTS

GB  1299367  12/1972

(Continued)

OTHER PUBLICATIONS

Packaging and instruction sheet for "umbillical hernia plaster" produced by Lohmann GmbH & Co., KG (Postflach 23 43, D-56513 Neuwied, Germany); undated.

(Continued)

*Primary Examiner*—Kim M Lewis
(74) *Attorney, Agent, or Firm*—Pierce Atwood LLP; Kevin M. Farrell; Katherine A. Wrobel

(57) ABSTRACT

Disclosed are methods for producing an interlaced device or composition which includes at least a first and a second interlaced element. Each interlaced element includes a mated first and second part, the first part having two termini and the second part having two termini, and a defined central void through which the other interlaced element passes. The method includes the processing and mating of a first and a second substrate layer, each including a top surface, a bottom surface and a mating zone. The first substrate layer includes a portion corresponding to a first part of a first interlaced element and a first part of a second interlaced element. The second substrate layer includes a portion corresponding to a second part of a first interlaced element and a second part of a second interlaced element. Also disclosed are interlaced devices or compositions.

39 Claims, 8 Drawing Sheets

U.S. PATENT DOCUMENTS

| | | |
|---|---|---|
| 3,645,835 A | 2/1972 | Hodgson |
| 4,112,213 A | 9/1978 | Waldman |
| 4,141,363 A | 2/1979 | James et al. |
| 4,310,509 A | 1/1982 | Berglund et al. |
| 4,323,557 A | 4/1982 | Russo et al. |
| 4,328,057 A | 5/1982 | Gutow |
| 4,374,520 A | 2/1983 | Grossmann |
| 4,413,621 A | 11/1983 | McCracken |
| 4,423,731 A | 1/1984 | Roomi |
| 4,472,480 A | 9/1984 | Olson |
| 4,485,809 A | 12/1984 | Dellas |
| 4,499,896 A | 2/1985 | Heinecke |
| RE31,887 E | 5/1985 | Hodgson |
| 4,524,095 A | 6/1985 | Gockel et al. |
| 4,545,371 A | 10/1985 | Grossmann |
| 4,549,063 A | 10/1985 | Ang |
| 4,587,146 A | 5/1986 | Anhauser |
| 4,590,022 A | 5/1986 | Cioca |
| 4,595,001 A | 6/1986 | Potter |
| 4,595,011 A | 6/1986 | Phillips |
| 4,596,738 A | 6/1986 | Metcalfe |
| 4,600,001 A | 7/1986 | Gilman |
| 4,614,183 A | 9/1986 | McCracken |
| 4,646,731 A | 3/1987 | Brower |
| 4,664,106 A | 5/1987 | Snedeker |
| 4,678,462 A | 7/1987 | Vaillancourt |
| 4,706,662 A | 11/1987 | Thompson |
| 4,737,410 A | 4/1988 | Kantner |
| 4,753,232 A | 6/1988 | Ward |
| 4,787,380 A | 11/1988 | Scott |
| 4,825,866 A | 5/1989 | Pierce |
| 4,830,914 A * | 5/1989 | Vaillancourt ............... 428/42.2 |
| 4,926,850 A | 5/1990 | Lott et al. |
| 4,950,282 A | 8/1990 | Beisang |
| RE33,353 E | 9/1990 | Heinecke |
| RE33,727 E | 10/1991 | Sims |
| 5,088,483 A | 2/1992 | Heinecke |
| 5,106,383 A | 4/1992 | Mulder |
| 5,135,518 A | 8/1992 | Vera |
| 5,160,315 A | 11/1992 | Heinecke |
| 5,176,703 A | 1/1993 | Peterson |
| 5,263,970 A | 11/1993 | Preller |
| 5,336,162 A | 8/1994 | Ota |
| 5,425,702 A | 6/1995 | Carn et al. |
| 5,531,855 A | 7/1996 | Heinecke et al. |
| 5,534,010 A | 7/1996 | Peterson |
| 5,685,833 A | 11/1997 | Turngren |
| 5,733,251 A | 3/1998 | Johns |
| 5,733,570 A | 3/1998 | Chen |
| 5,738,642 A | 4/1998 | Heinecke et al. |
| 5,779,659 A | 7/1998 | Allen |
| 5,849,325 A | 12/1998 | Heinecke |
| 5,891,078 A | 4/1999 | Turngren |
| 5,979,450 A | 11/1999 | Baker et al. |
| 5,981,823 A | 11/1999 | Turngren |
| 6,129,971 A | 10/2000 | Brandt |
| 6,149,614 A | 11/2000 | Dunshee |
| 6,169,224 B1 | 1/2001 | Heinecke |
| 6,264,976 B1 | 7/2001 | Heinecke |
| 6,329,564 B1 | 12/2001 | Lebner |
| 6,364,188 B1 | 4/2002 | Dunshee |
| 6,420,622 B1 | 7/2002 | Johnston |
| 6,436,432 B2 | 8/2002 | Heinecke |
| 6,461,467 B2 | 10/2002 | Blatchford |
| 6,495,230 B1 | 12/2002 | do Canto |
| 6,548,727 B1 | 4/2003 | Swenson |
| 6,566,575 B1 | 5/2003 | Stickels |
| 6,596,917 B2 | 7/2003 | Oyaski |
| 6,607,799 B1 | 8/2003 | Heinecke |
| 6,822,133 B2 | 11/2004 | Lebner |
| 6,831,205 B2 | 12/2004 | Lebner |
| 6,982,359 B1 | 1/2006 | Beaudry |
| 2004/0106888 A1 | 6/2004 | Lutri et al. |
| 2004/0204740 A1 | 10/2004 | Weiser |
| 2004/0243040 A1 | 12/2004 | Weiser |
| 2005/0182443 A1 | 8/2005 | John |

FOREIGN PATENT DOCUMENTS

WO    WO2005/079674 A1    1/2005

OTHER PUBLICATIONS

Stalar: "A more effective way to wound closure," by S. Paris, Abstract, Pub. by 43 Intern'l Sci. and Eng. Fair, Nashville, Tennessee, May 10, 1992, p. 257.

Paris, Stacy: "Is there a more effective way to accomplish wound closure than those presently employed?"; author indicates abstract published by South Carolina Junior Academy of Science, Feb. 1991; applicants have not independently verified this publication date.

* cited by examiner

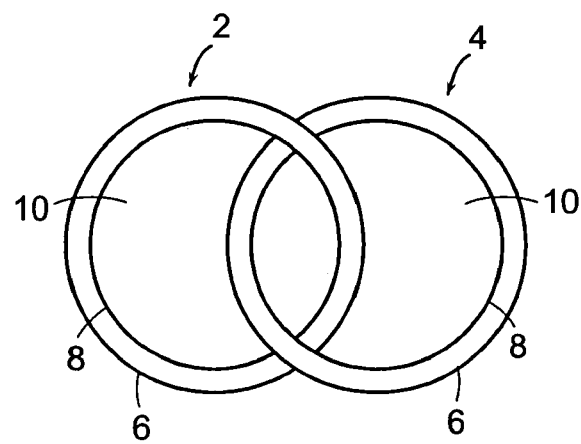
FIG. 1
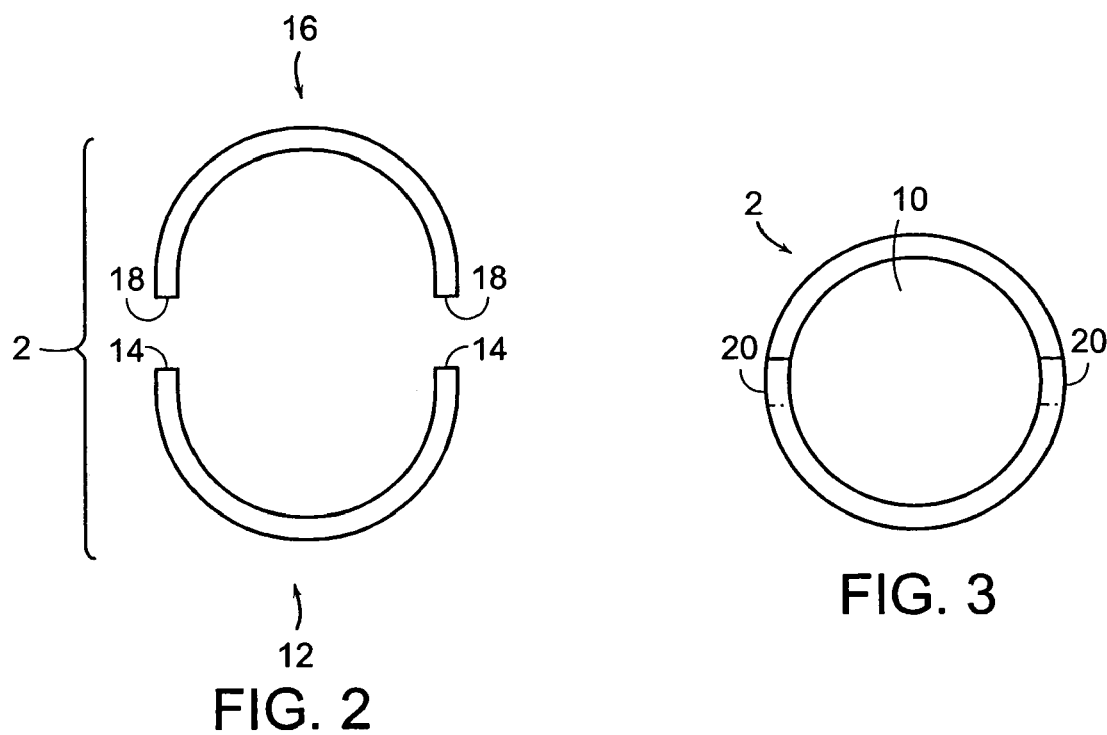
FIG. 2
FIG. 3

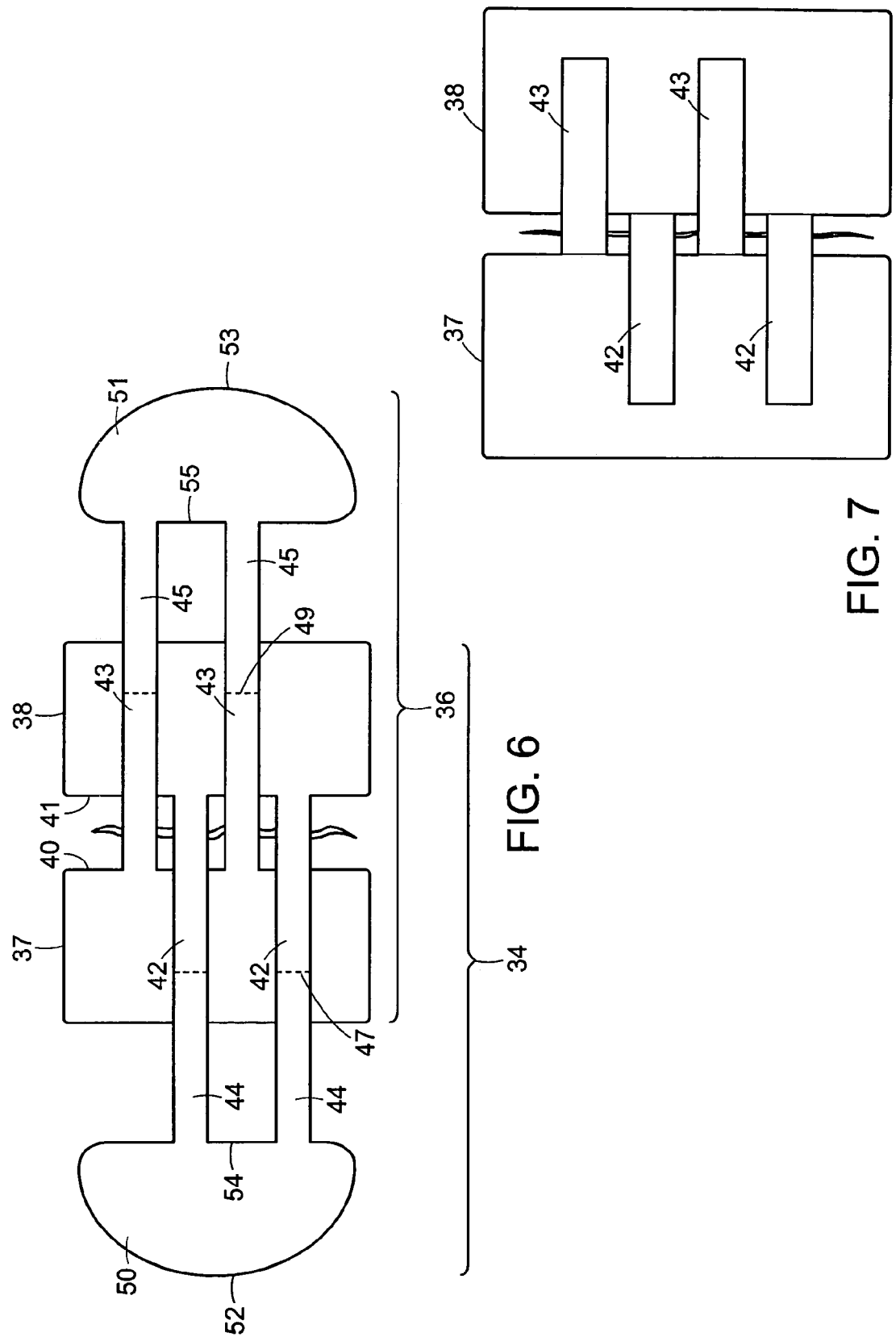

INTERLACED COMPOSITIONS AND METHODS OF PRODUCTION

BACKGROUND OF THE INVENTION

U.S. Pat. No. 6,329,564, the disclosure of which is incorporated herein by reference, discloses an interlaced, two-component wound closure device. Disclosed methods for interlacing the two components of the prior art device were: 1) producing at least one component as an incomplete component, interlacing the two components, then completing the incomplete component; and 2) producing two individual components, cutting one to enable interlacing, then repairing the cut (e.g., using adhesive tape). Neither of these alternative methods for producing an interlaced two-component wound closure device is entirely satisfactory. The primary deficiency associated with prior art methods for producing an interlaced device of this type is the requirement for manual assembly as described above. Thus, while individual elements can be die cut, for example, in a cost-effective manner, manual assembly of the individual elements is an expensive and time-consuming activity. A method for producing an interlaced device which does riot suffer from this deficiency would represent a significant advance in the manufacturing process.

SUMMARY OF THE INVENTION

The present invention relates to a method for producing an interlaced device which includes a first and a second interlaced element. Each interlaced element includes a mated first and second part, the first part having two termini and the second part having two termini, and a defined central void through which the other interlaced element passes. The method includes the processing and mating of a first and a second substrate layer, each including a top surface, a bottom surface and a mating zone. The first substrate layer includes a portion corresponding to a first part of a first interlaced element and a first part of a second interlaced element. The second substrate layer includes a portion corresponding to a second part of a first interlaced element and a second part of a second interlaced element.

A series of terminal end cuts are introduced in the first substrate layer for the first part of the first interlaced element and the first part of the second interlaced element. Cross-over point cuts are introduced in the first substrate layer for the first part of the first interlaced element and the first part of the second interlaced element. Similarly, terminal end cuts are made in the second substrate layer for the second part of the first interlaced element and the second-part of the second interlaced element. Additionally, cross-over point cuts are made in the second substrate layer to define a cross-over point of the second part of the first interlaced element and a cross-over point of the second part of the second interlaced element.

Following the introduction of these essential cuts, the top surface of the first substrate layer is mated to the bottom surface of the second substrate layers by aligning the mating zones and interlaced element parts. The mated substrate layers are bonded along the mating zones. Any necessary cuts are completed to fully define the first and second interlaced elements.

Embodiments of the present invention also include modifications of the previously described method which relate to the production of an interlaced device having at least two interlaced elements.

The present invention also relates, in one aspect, to an interlaced wound closure device comprising two interlaced elements. Each interlaced element of the wound closure device is produced from two or more substrate layers and includes a plurality of overlapping and bonded portions at which the two or more substrate layers are joined to form an interlaced element. Each interlaced element further includes an adhesive-backed anchoring element having a substantially linear wound edge, a plurality of connecting elements extending from the wound edge in a first direction and a pulling element attached to the connecting elements. In preferred embodiments, at least a portion of the lower surface of the connecting elements are adhesive-backed. Specific methods for producing an interlaced wound closure device of this type are also disclosed.

BRIEF DESCRIPTION OF THE DRAWINGS

FIG. 1 is a top view representing two interlaced rings.

FIG. 2 is a top view representing one interlacing ring showing two constituent portions.

FIG. 3 is a top view representing one interlacing ring showing a mating zone, or area of overlap, between two constituent portions of the ring.

FIG. 6 is a top view of an interlaced wound closure device of the present invention which includes removable portions of connecting elements and pulling elements.

FIG. 7 is a top view of an interlaced wound closure device of the present invention in an applied state in which removable portions of connecting elements and pulling elements have been separated from the device.

DETAILED DESCRIPTION OF THE INVENTION

Figure 4:
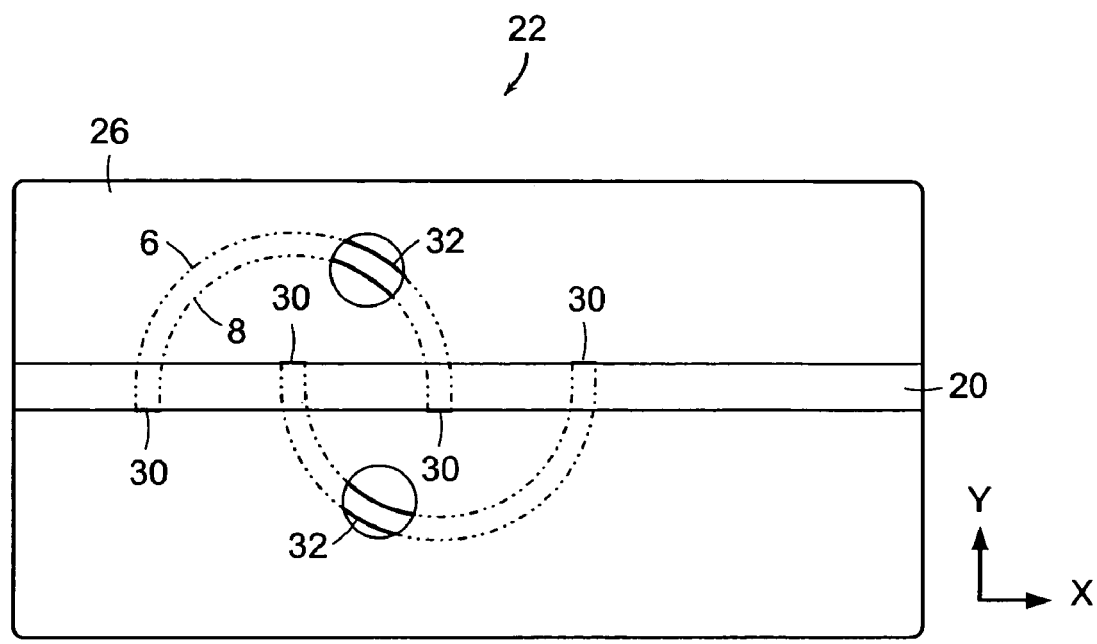
FIG. 4 is a top view representing minimum essential cuts (solid lines) to be made in a top substrate layer prior to mating with a bottom substrate layer followed by additional processing.

The present invention relates, in one aspect, to a method for producing an interlaced device. The term "interlaced device", as used herein, refers to a device or object which includes two or more interlaced elements. FIG. 1 represents a simple interlaced device which includes two rings or interlacing elements (2 and 4). The terms "interlacing elements" and "interlaced elements" may be used interchangeably herein. In the interlaced device, each interlaced element includes a continuous outer perimeter (6) and a continuous inner perimeter (8). The continuous inner perimeter (8) defines a central void (10) in an interlaced element through which another interlaced element passes. Thus, the interlaced elements are connected in a manner similar to links in a chain. There is no requirement of uniformity of shape for the interlaced elements.

Conventionally, interlaced devices of the type to which the present manufacturing method applies, are produced by linking individual interlacing elements (i.e., elements to be interlaced) by: 1) forming a closed interlacing element (e.g., a chain link); 2) passing through the closed interlacing element a second interlacing element; and 3) closing the second interlacing element. For example, continuing with the chain manufacturing example, a first link is produced by bending a heated, precisely cut portion of meal rod to the shape of the first link. The adjacent ends are butt welded to complete the first link. The second link is produced by passing a second, substantially identical cut and heated portion of metal rod through the first link, followed by bending and butt welding. This is a time consuming process, but there is no alternative process available for chain manufacturing.

The present invention relates to the production of interlaced devices from sheet, roll or other layer stock. The term "substrate layer" is used herein to describe any suitable material for use in connection with the disclosed methods. Examples of sheet or layer stock include polymer (plastic), sheet metal, foils, textile and hide materials. The essential feature of the sheet or layer stock for use in connection with the present invention is that the material must be amenable to cutting (e.g., using knives, punches, or laser trimming devices). Additionally, for use in connection with the present invention, cut portions in at least two sheets or layers must be brought into proximity and joined or mated. It is not essential that the substrate layers be of identical stock.

Considering the method in greater detail, FIG. 2 represents an interlacing element (2) drawn to show constituent halves. The interlacing element (2) includes a first part (12) having two termini (14) and a second part (16) having two termini (18). The first part (12) and the second part (16) of interlacing element (2) are cut from separate substrate layers. As shown in FIG. 3, the two parts of interlacing element (2) are mated along a mating zone (20) to define a central void (10) through which another interlaced element passes. The method of the present invention enables the automated production of an interlaced device from two or more substrate layers using manufacturing techniques such as die cut manufacturing. The substrate layers may also be provided in roll form enabling even more efficient automated manufacturing of the interlaced devices and theoretically the ability to manufacture interlaced devices of unlimited length.

Figure 5:
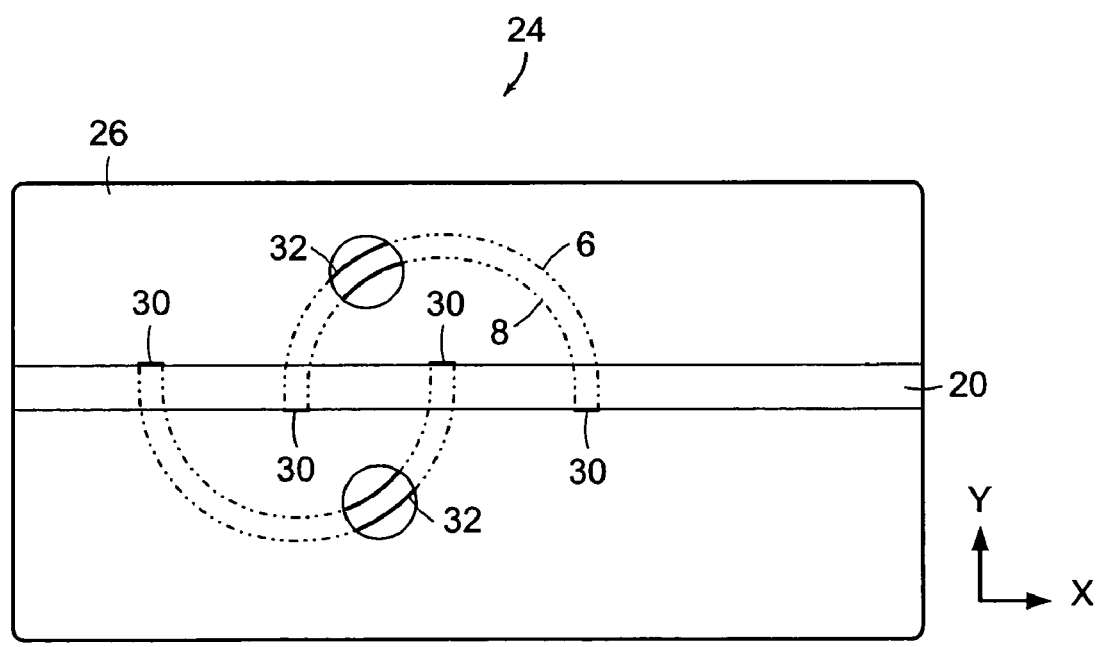
FIG. 5 is a top view representing minimum essential cuts (solid lines) to be made in a bottom substrate layer prior to mating with a top substrate layer followed by additional processing.

For the production of an interlaced device of the type shown in FIG. 1 which includes only a first (2) and a second (4) interlaced element, two substrate layers are used. First and second substrate layers, satisfying the criteria discussed above, are initially provided. Referring to FIGS. 4 and 5, the substrate layers are drawn as sheets, for simplicity of illustration. The top substrate layer (22) and the bottom substrate layer (24) each include a top surface (26), a bottom surface (not shown), and a mating zone (20). The first substrate layer includes portions to be cut to form the first part of the first interlaced device and the first part of the second interlaced device (shown in phantom in FIG. 4). The second substrate layer includes portions to be cut to form the second part of the first interlaced element and the second part of the second interlaced element (shown in phantom in FIG. 5). It will be recognized that a plurality of interlaced devices, each having a first and a second interlaced element, can be produced using two substrate layers by repeating the steps described below in series along the substrate layers.

The preceding paragraph refers to portions of the first and second substrate layers "to be cut" to produce specific device parts. An important feature of the invention, however, lies in the extent and timing of the cuts required to produce the device. A subset of the cuts required to produce the interlaced element include two species of cuts that must be made in each substrate layer before they are mated and the post-mating cuts are introduced. These cuts are referred to herein as "essential cuts". For the simple interlaced ring example, essential cuts made in the top (22) and bottom (24) substrate layers individually are represented in FIGS. 4 and 5, respectively.

Essential cuts in each substrate layer include the terminal end cuts (30) of the first and second parts of each interlaced element (i.e., 8 individual cuts). As discussed above, each interlaced element includes a continuous outer perimeter (6) and a continuous inner perimeter (8) (shown in phantom in FIGS. 4 and 5). The continuous inner perimeter (6) defines a central void in an interlaced element through which another interlaced element passes. The term "terminal end cut" (30), as used above, refers to cuts in those end portions of the four parts (in the embodiment described) of an interlaced device that bridge or connect the cuts which form the continuous outer perimeter (6) and the continuous-inner perimeter (8) of the completed interlaced element. Although the terminal end cuts (30) in the example provided are straight cuts along the boundary of the mating zone (20), this is not a requirement.

Essential cuts in the first and second substrate layers also include "cross-over point cuts" (32) in the four parts of each interlaced device. In FIGS. 4 and 5, the circle over cross-over point cuts (32) is intended to represent a zone of magnification. The term "cross-over point" refers to those portions of the four parts of the interlaced device which define the outer and inner perimeters of a part at the point of non-bonded overlap with another part following the mating of the two substrate layers.

Another way of specifying the essential cuts (i.e., cuts made prior to mating the two substrate layers) is to define these functionally. The essential cuts which must be made prior to mating the two substrate layers are those which can not be made through both substrate layers following mating Without adversely affecting the integrity of the interlaced device. The "terminal ends cuts" (30) can not be made following mating because such cuts, if made through both layers, would create a gap or break in each interlaced element thereby rendering the elements non-interlaced. The "cross-over point" cuts (32) can not be made following mating because such cuts (if made through both substrate layers following mating) would also create a gap or break in each interlaced element.

In the embodiment represented in FIGS. 4 and 5, after introducing the terminal end cuts (30) and cross-over point cuts (32) for all four parts of the interlaced device, the first and second substrate layers are aligned in two dimensions and joined along a mating zone (20). The alignment in two dimensions includes: 1) a Y-dimension alignment in which the mating zone of the top substrate layer is placed directly over the mating zone of the bottom substrate layer; and 2) an X-dimension alignment to place portions of the top substrate layer (22) to be cut to form a first part of a first interlaced element in overlapping relation with portions of the bottom substrate layer (24) to be cut to form a second part of a first interlaced element. Following the alignment of the substrate layers in two dimensions, the two substrate layers are bonded along the mating zone. The bonding of the two substrate layers along the mating zone can be accomplished in a number of ways including, for example, through the use of adhesive, ultrasonic welding, or fastening or bonding means (e.g., hook and loop fastening or riveting).

In the mated assembly, terminal end cuts (30) at the boundary of the mating zones (20) outline the two areas of overlap between the first part of the first interlacing element and the second part of the first interlacing element. Taking FIGS. 4 and 5, for example, terminal end cuts (30) in mated top substrate layer (22) and bottom substrate layer (24) define the areas of overlap, in the Y-dimension, between the first part of the first interlacing element and the second part of the first interlacing element. Similarly, terminal end cuts (30) at the boundary of the mating zone (20) outline (in the Y-dimension) the two areas of overlap between the first part of the second interlacing element and the second part of the second interlacing element. The word "outlines" is intentionally used in the preceding sentences because outer and inner perimeter cuts are required to fully define the areas of overlap mentioned (in the X-dimension in the example provided).

As discussed above, terminal end cuts (30) and cross-over point cuts (32) are the essential cuts which are required to be made prior to mating of the two substrate layers (22 and 24 in FIGS. 4 and 5). To fully form the simple interlaced element represented in FIG. 1, the complete outer perimeter (6) and complete inner perimeter (8) as shown in phantom in FIGS. 4 and 5 must be cut. While the essential cuts must be made prior to mating, other portions of the outer and inner perimeters may be cut either before, or after mating. It is desirable that cuts made across the mating zone which fully define the portion of bonded overlap between the interlaced elements be made after mating of the two substrate layers. The reason for this preference is that a single cut passing through both substrate layers will define the outer perimeter of the bonded portion and a single cut through both substrate layers will define the inner perimeter of the bonded portion. Another essential consideration in determining the timing of the various cuts is stability of the web (i.e., the sheet or roll stock containing a series of interlacing element parts or portions to be cut to form parts). The introduction of excessive non-essential cuts prior to mating can interfere with stability of the substrates and their proper alignment. A significant benefit of the present method is that it enables automated production from rolls of stock. As the rolls are feeding through a die cut press machine, for example, it is important that the parts being cut from the roll are stable (i.e., they do not fold over, tear, or in any other way impact the production rate, generate non-usable devices or excessive scrap). Thus, it is preferable that substantial non-essential cuts in both the top and bottom layers be reserved for final stage (i.e., post mating) processing.

It will be recognized by one of skill in the art that the principles discussed above in connection with an interlaced device comprising two interlaced elements can be extended to complex interlaced assemblies comprising more than two interlaced elements. More complex embodiments may be produced from more than two substrate layers and may involve the use of more than one mating zone.

Interlaced devices produced according to the methods disclosed herein are useful in a variety of contexts. For example, linear constructions comprising a long series of interlaced elements may be used for decorative purposes, or structurally as an alternative to light chain (e.g., for hanging lighting fixtures). Simpler devices, such as a two-component device having a first and second interlaced element can be used as a closure device useful for easily and precisely altering the spatial relationship between two surfaces, or two portions of a single surface.

Use of an interlaced device produced by the disclosed methods for purposes of altering the spatial relationship between two surfaces (or portions of a single surface) can be accomplished by attaching a portion of one interlaced element to one surface, and a portion of the second interlaced element to a second surface. This can be exemplified by considering the use of the disclosed method for the purposes of producing a wound closure device of the type shown in FIG. 6. The preferred embodiment of the wound closure device includes two interlaced elements (34 and 36). Each of the interlaced elements includes an anchoring element (37, 38) for attachment to the skin of an individual. Preferably the anchoring element (37, 38) is adhesive backed for convenient and secure attachment to the skin. The anchoring elements include a substantially linear wound edge (40 and 41).

Each interlaced element includes a plurality of connecting elements (42 and 43) extending from the wound edges (40 and 41) of each of the anchoring elements (37 and 38) in a direction which is substantially perpendicular to the associated wound edge. In preferred embodiments, connecting elements (42 and 43) include removable portions (44 and 45). A perforation (47 and 49) is optionally provided to facilitate removal of the removable portions (44 and 45) of connecting elements (42 and 43) after the desired positioning is achieved. Pulling elements (50 and 51) are provided, each pulling element (50 and 51) having an outer edge (52 and 53) and an inner edge (54 and 55). The inner edges (54 and 55) of the pulling elements (50 and 51) are attached to the connecting elements (42 and 43), or removable portions thereof (44 and 45). The pulling elements (50 and 51) are used to pull the wound edges (40 and 41) toward each other, thereby closing the wound or incision.

In use, one anchoring element (e.g., 37) is positioned on one side of a laceration or incision. The second anchoring element (e.g., 38) is then positioned on the other side of the laceration or incision. Pulling elements (50 and 51) are then pulled in opposing direction to close the laceration or incision. Following closure, the position of the first and second interlaced elements (34 and 36) are fixed relative to one another. This is accomplished by attaching the connecting members (e.g., 42) of one interlaced element (34) to the anchoring member (37) of the other interlaced element (36). Adhesive is preferably provided for attaching the connecting elements of one interlaced element to the anchoring element of the other interlaced element. Preferably, this adhesive is applied to the lower surfaces of connecting members (42 and 43). It is preferred that the lower surfaces of connecting members (42 and 43) which are directly over a laceration or incision following application of a device be adhesive-free. The term "adhesive-free" is intended to include areas in which an adhesive layer is provided, and subsequently blocked by the application of an adhesive-kill layer (e.g., polyester).

FIG. 7 represents the device following wound closure and attachment of connecting members (43) to anchoring element (38) and connecting members (42) to anchoring element (37). Following attachment of the device, as shown in FIG. 7, pulling elements (50 and 51) and removable portions of connecting elements (44 and 45) are removed to minimize the space occupied by the applied device for increased comfort and security, As has been indicated above in connection with the simple, two ring interlaced device, each interlaced element will have two points of overlap between the first and second part which make up the interlaced element. In the wound closure device of the present invention, these points of overlap are preferably located on the over-wound bridging portion of the connecting members (42 and 43) (i.e. the portion of the connecting members bridging the two anchoring elements as shown in FIG. 7). Although not shown in FIG. 7, the over-wound bridging portion is preferably more narrow than the portion of the connecting elements (42 and 43) which are actually attached to an anchoring element (37 or 38). This narrowing is intended to maximize wound exposure thereby promoting exudate drainage and facilitating the application of medications. The narrowing also enables greater lateral adjustment of the device because narrowing the connecting elements in the over-wound area effectively increases the spacing between adjacent connecting elements. Narrowing of the over-wound bridging portion of connecting members (42 and 43) could possibly create a weak point in the interlaced elements, and providing for the bonded overlap of the constituent parts in this area increases the holding power of the device.

Figure 8:
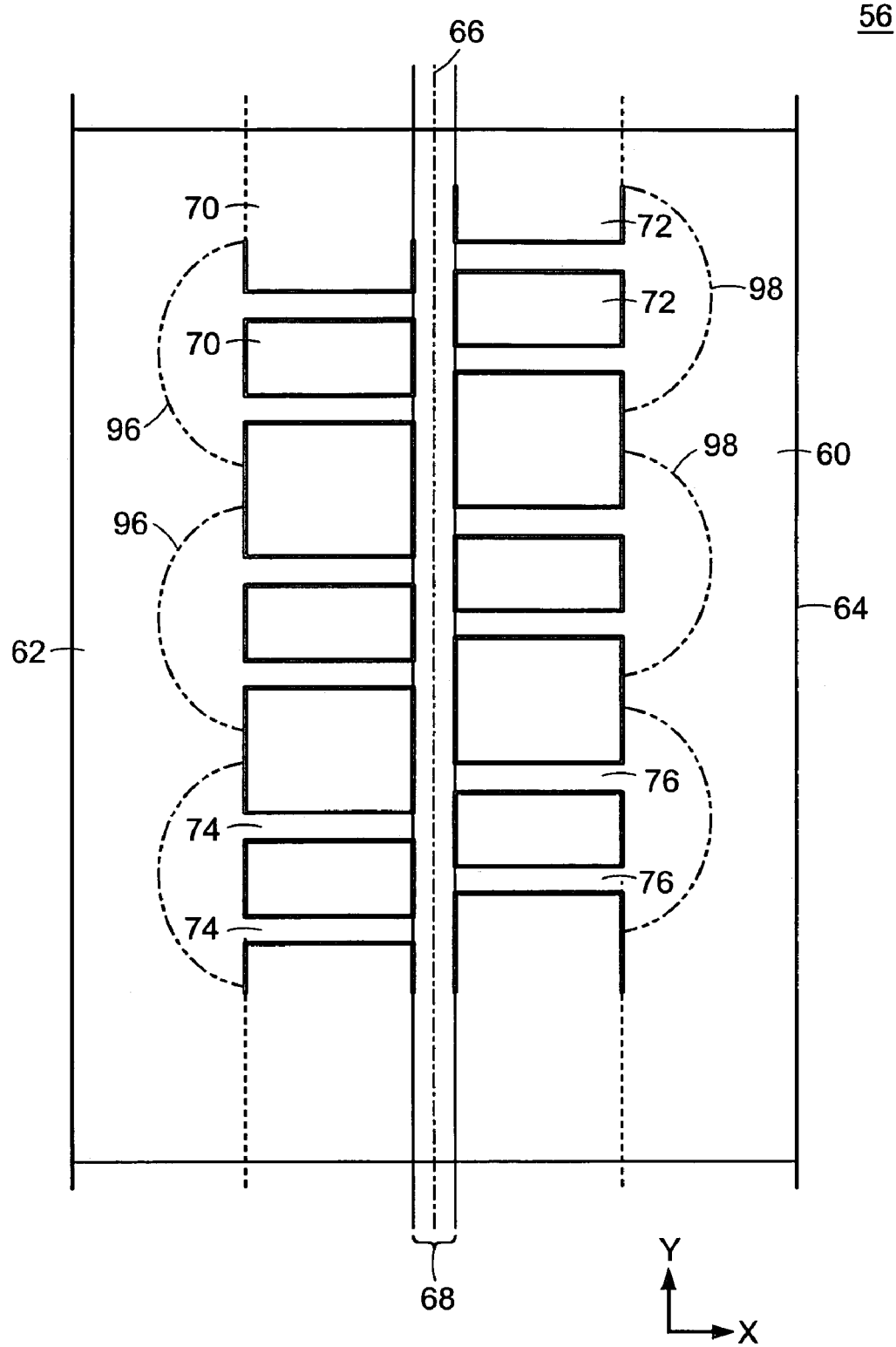
FIG. 8 is a top view of a bottom substrate layer showing a first and second series of parallel cut-outs representing an intermediate stage in a disclosed method of producing an interlaced device.
Figure 9:
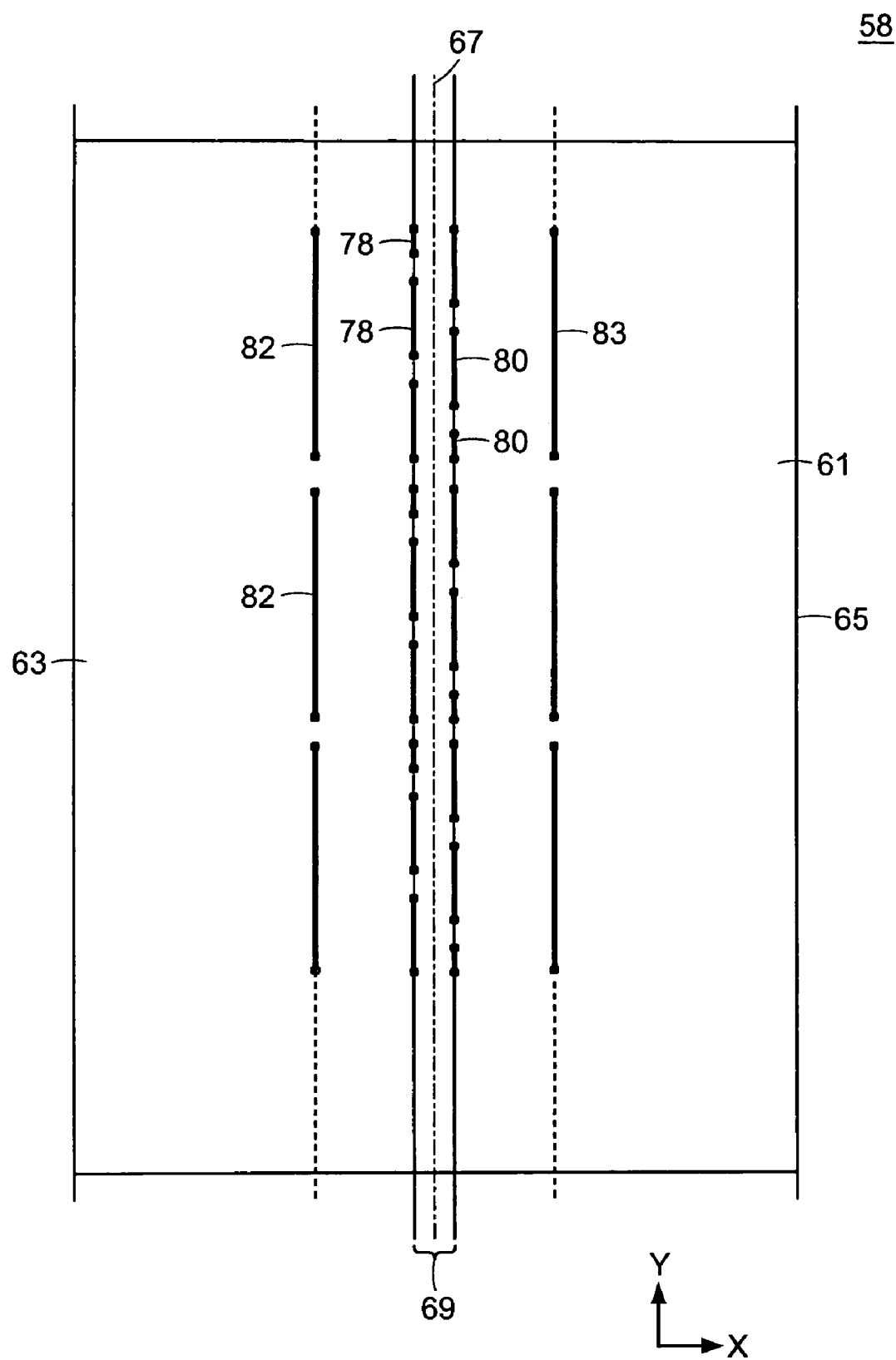
FIG. 9 is a top view of a top substrate layer showing four series of parallel slits representing an intermediate stage in a disclosed method of producing an interlaced device.

Having described the device to be produced by the present manufacturing method, the method itself will now be described. Application of the presently disclosed manufacturing methods to the production of the wound closure device described above enables mass production at substantially reduced cost relative to earlier production runs which required manual assembly. Referring to FIGS. 8 and 9, a preferred production method for manufacture of the interlaced wound closure components (with no associated release liners or adhesive on anchoring elements and connecting elements) includes the following steps. A first (56) and second (58) (bottom and top, respectively) substrate layer is provided. Each layer has a top surface (60 and 61), a bottom surface (not shown), a left edge (62 and 63), a right edge (64 and 65) and a center line (66 and 67) shown bisecting mating zones (68 and 69). These substrate layers are preferably flexible polymeric materials, scrims or fabric reinforced substrates or films. One skilled in the art will be familiar with a variety of such materials suitable for a given application. The selection of a particular material from among the options available would be a matter of design choice. For use in wound closure devices, it is preferable that these polymeric materials are substantially inelastic, or are reinforced in critical areas for which the inelastic property is particularly important (i.e., the connecting elements).

Referring to FIG. 8, two parallel series of cut-outs are made in the bottom substrate layer. The first parallel cut-out series extends (70) from the left edge of the mating zone (68) toward the left edge (62) of the bottom substrate layer (56). The second parallel cut-out series (72) extends from the right edge of the mating zone (68) toward the right edge (64) of the bottom substrate layer (56). The portion of the bottom substrate layer (56) remaining left of the mating zone (68) between cut-outs in the first series of parallel cut-outs (70) defines the connecting members (74) of a series of first components. The portion of the bottom substrate layer (56) remaining right of the mating zone (68) between individual cut-outs (72) in the second series of parallel cut-outs defines the connecting members (76) of a series of second components.

Additional cuts in the bottom substrate layer (56) between cut-outs 70 and left edge (62) are made to form pulling elements. For example, arcuate cuts 96 and 98 are examples of such cuts which will produce pulling elements in the completed wound closure device. It will be recognized by one skilled in the art that although arcuate cuts 96 and 98 may be made either before or after mating of the top and bottom substrate layer, it is highly desirable that these cuts be made in the final stages of processing following mating of the top and bottom substrate layers (56 and 58). The reason for this preference is because the introduction of arcuate cuts (96 and 98) (if made following the introduction of the first and second parallel cut-out series (70 and 72) complete the entire inner and outer perimeter of the device portions to be cut from the bottom substrate layer (56). This is undesirable in early stages of processing, especially pre-mating, in light of the fact that substantially complete portions of pulling elements and connecting elements would be free to separate from the processing web resulting in a high failure rate.

Referring to FIG. 9, the top substrate layer (58) is processed by cutting a first and second series of slits (78 and 80, respectively) along the left and right edge of the mating zone (69). The first and second series of slits (78 and 80) define the wound edges (40 and 41 as best seen in FIG. 6) of the to-be-formed first and second anchoring elements. Discontinuities in the first and second series of cuts (78 and 80) correspond to to-be-formed connecting members or spacing between individual devices in the processing web. A third series of slits (82) is cut through the top substrate layer (58) to define an outer edge of a series of anchoring elements, the third series of cuts being generally parallel the associated wound edge series formed by the first series of slits (78). A fourth series of slits (83) is cut through the top substrate layer to define an outer edge of a second series anchoring elements, the fourth series of slits being (83) generally parallel to the second series of slits (80) defining the wound edge of the second series of anchoring elements.

The top and bottom substrate layers (56 and 58) are then aligned in two dimensions, as was described for the simpler, two ring example discussed above. The mating zones (68 and 69) of the bottom substrate layer (56) and the top substrate layer (58) are aligned in an X-dimension. In a Y-dimension, discontinuities in the first series of slits (78) are aligned in register with connecting elements (74) formed by cutting the first series of parallel cut-outs (70) in bottom substrate layer (56). The alignment in two dimensions brings the to-be-formed devices into registration, and the top surface of the bottom substrate layer (56) is mated with the bottom surface of the top substrate layer (58). The top and bottom substrate layers are bonded along the aligned mating zones (68 and 69). Bonding can be accomplished through the use of a pre-applied adhesive, ultrasonic welding or other fastening or bonding means.

Following bonding along the aligned mating zones (68 and 69), cuts are introduced through the layers of the bonded mating zone which will serve to fully define the connecting members at the point at which they meet their associated anchoring element. Two cuts across the mating zone (68 and 69), and through both substrate layers (56 and 58), are required for each connecting member. Each of these cuts must intersect with a pre-existing cut in each substrate layer (56 and 58) on each side of the mating zone (68 and 69). Referring specifically to bottom substrate layer (56) (see FIG. 8), two cuts must be made across mating zone (68) to extend each connecting member (74 and 76) across the mating zone (68).

Figure 10:
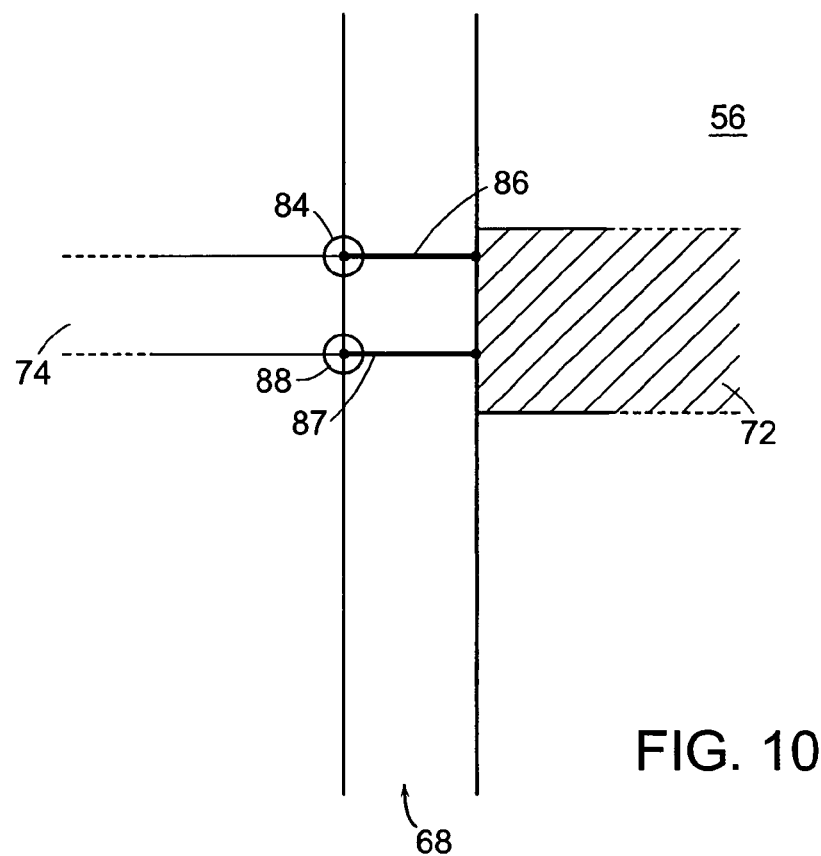
FIG. 10 is a top view of a bottom substrate layer showing detail relating to two cross-mating zone cuts.

The detail of this cut is illustrated in FIG. 10. FIG. 10 is a top view of mated bottom substrate layer (56), with its mate, top substrate layer (58) not shown. FIG. 10 represents a portion of a connecting element (74) at the point where it meets mating zone (68). Also shown, on the opposing side of mating zone (68) is one cut-out from the second parallel cut-out series (72). The two cuts required to fully define the connecting member are shown as a first and second cross-mating zone cut (86 and 87). On the left side of the mating zone (68) cut (86) intersects with the cut made to form connecting member (74). Preferably, as shown, cut (86) intersects with the cut made to form connecting member (74) at a first corner (84). If cut (86) were made inboard of the first corner (84), a weak point in the connecting member would result. On the right side of the mating zone (68), cut (86) intersects with the cut made to form the second parallel cut-out series (72). Similarly, the second cross-mating zone cut (87) preferably intersects with the line cut to form connecting member (74) at a second corner (88) and extends across mating zone (68) and intersects with the cut made to form the second parallel cut-out series (72). Thus, cuts (86 and 87) terminate at the right side of the mating zone within a previously cut-out portion (72). The net effect of the two cuts (86 and 87) in the bottom substrate layer (56) is to extend the connecting member 74 across the mating zone (68), at which point it is terminated. A similar series of two cuts are made across the mating zone (68) to similarly extend each connecting member (74 and 76) across the mating zone (68).

Figure 11:
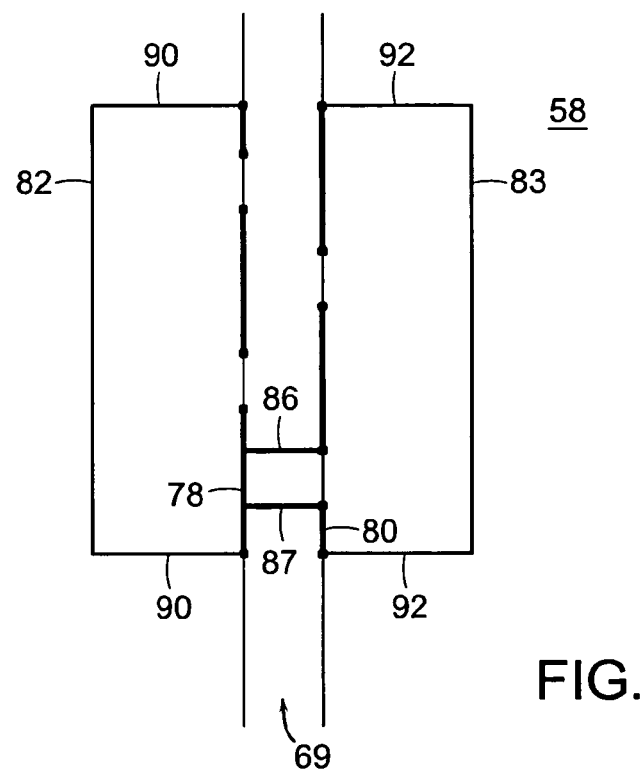
FIG. 11 is a top view of a top substrate layer showing detail relating to two cross-mating zone cuts.

FIG. 11 shows the same two cuts (86 and 87) in top substrate layer (58). Cuts 82 and 83 were previously shown in FIG. 9 and refer to individual slits in a third and fourth series of slits previously described. Slits 82 and 83 define the outer edges of two anchoring elements to be assembled in a single interlaced wound closure device. The first and second slit series (78 and 80) were previously shown and described in connection with FIG. 9. A subset of the discontinuities in first slit series 78, as shown in FIG. 11, correspond to the area at which connecting member (43) meets anchoring element (37) as best seen in FIG. 6. Similarly, a subset of the discontinuities in second slit series (80) correspond to the area at which connecting members 42 meet anchoring element (38) as best seen in FIG. 6. Cuts (86 and 87), shown in FIG. 11, intersect two previously made cuts in top substrate layer (58). Specifically, on the left side of mating zone (69), cut (86) intersects with a non-terminal portion of a slit in the first series of slits (78). On the right side of mating zone (69), cut (86) intersects with a terminal portion of slit series (80) which defines the beginning of the area at which connecting member (42) meets anchoring element (38) (as best seen in FIG. 6). Cut (87) intersects the same slit in the first series of slits as cut (86). On the right side of the mating zone (69), cut (87) intersects with a terminal portion of a slit from slit series (80) which defines a second side of connecting member (42) at the point where it meets anchoring element (38) as best seen in FIG. 6.

Following the completion of mating zone cuts which fully define the connecting members (42 and 43) at the point of attachment to the anchoring elements (37 and 38), the remaining cuts required are those to complete the formation of the anchoring elements (37 and 38). FIG. 11 shows anchoring element end cuts (90 and 92) which complete the formation of the anchoring elements. While these cuts are made through both layers (56 and 58), only the cuts in the top substrate layer (58) are involved in shaping the device. The cuts through the bottom substrate layer (56) are incidental only. Following the completion of the cuts described above, the interlaced device is complete.

In a completed wound closure device, preferred embodiments include adhesive on the lower surfaces of anchoring elements and portions of connecting elements of an interlaced element which contact the anchoring element of another interlaced device following closure of the incision or laceration.

An example of a method for producing the device with adhesive in appropriate locations is included for guidance. Initially, the top surface of the bottom substrate layer (e.g., 60 in FIG. 8) is coated with a first adhesive layer suitable for attaching a connecting element to an anchoring element when the device is in use. Many such adhesive are known in the art and selection from among those available is merely a matter of design choice. In preferred embodiments, an adhesive-kill layer is applied to the portions of the first adhesive layer which will comprise the to-be-formed first and second pulling elements, and removable portions of connecting elements. It will be recognized that an alternative to whole-sheet adhesive application, followed by zone-coating with an adhesive-kill layer, is the zone-coating with an adhesive layer. Technical consideration, however, favor the two-step approach. It will also be recognized by one skilled in the art that removal of pulling elements and portions of connecting elements is not a requirement. To the extent that additional closure security is desirable, the adhesive-kill layer can be omitted and adhesive surfaces would extend to portions which are removed in preferred embodiments.

Referring again to FIG. 8, a first release liner (not shown) is applied along the left edge (62) of the bottom substrate layer (56), the first release liner extending from the left edge (62) of the bottom substrate layer (56) toward the center line (66) of the bottom substrate layer (56) and terminating at a point near the center line which defines the left edge of the mating zone (68). A second release liner (not shown) is applied along the right edge (64) of the bottom substrate layer (56). The second release liner extends from the right edge (64) of the bottom substrate layer (56) toward the center line (66) of the bottom substrate layer (56) and terminates at a point near the center line (66) which defines the right edge of the mating zone (68). A third release liner (not shown) is applied along the mating zone of the bottom substrate layer (56). As described in detail above, two parallel series of cut-outs are made in the bottom substrate layer and the attached release liners to the left and right side of the mating zone (68).

Referring again to FIG. 9, the top substrate layer (58) is processed by applying an adhesive layer (also referred to as the "second adhesive layer") to the top surface of the top substrate layer (61). An adhesive-kill layer (e.g., polyester, polycarbonate or release coating) is applied to a portion of the second adhesive layer comprising the mating zone (69). A release liner (also referred to as the "fourth release liner") (not shown) is applied to the portion of the second adhesive layer exposed to the left side of the mating zone. A release liner (also referred to as the "fifth release liner") (not shown) is applied to the portion of the second adhesive layer exposed to the right side of the mating zone (69). Mating the top and bottom substrate layers, and processing the layers as previously described, produces a series of wound closure devices having appropriately located adhesive with protective release liners.

A further improvement of the present invention relates to the application of a strip of semi-rigid material (preferably a polymeric material) to the top substrate layer which covers the mating zone, and extends partially over the portion of the top substrate layer which is cut to form the anchoring elements. In preferred embodiments, the strip of semi-rigid material fully covers the mating zone of the top substrate layer and extends over approximately half of the area to be processed to form the anchoring elements. Preferably this strip of semi-rigid material is applied to the top substrate layer after the mating of the top and bottom substrate layers and the introduction of cross-mating zone cuts (see 86 and 87 in FIGS. 10 and 11). It is further preferred that the strip of semi-rigid material be applied to the top substrate layer before the completion of the cuts which fully define the interlaced device. The reason for this preference is that the strip of semi-rigid material will serve to maintain the "as manufactured" relationship of the interlaced elements of an interlaced device until just prior to application of the device.

The application of a strip of adhesive on each side of the mating zone, and extending partially over the area of both sides of the mating zone which is to be cut to form the anchoring elements, provides a suitable means for attaching the strip of semi-rigid material. Release liners are optionally used to protect these strips of adhesive prior to the application of the strip of semi-rigid material. When applied, the two long edges of the strip of semi-rigid material are parallel with the edges of the mating zone of the top substrate layer. Prior to application, the strip of semi-rigid material is incompletely cut in the area to be applied over the mating zone, the incomplete cut being manually severable following completion of the manufacturing process. This incomplete cut forms a frangible line extending along the length of the strip of semi-rigid material. Preferably, the cut forming the frangible line is serpentine in shape to increase the length of the gripping edge during application.

Figure 12:
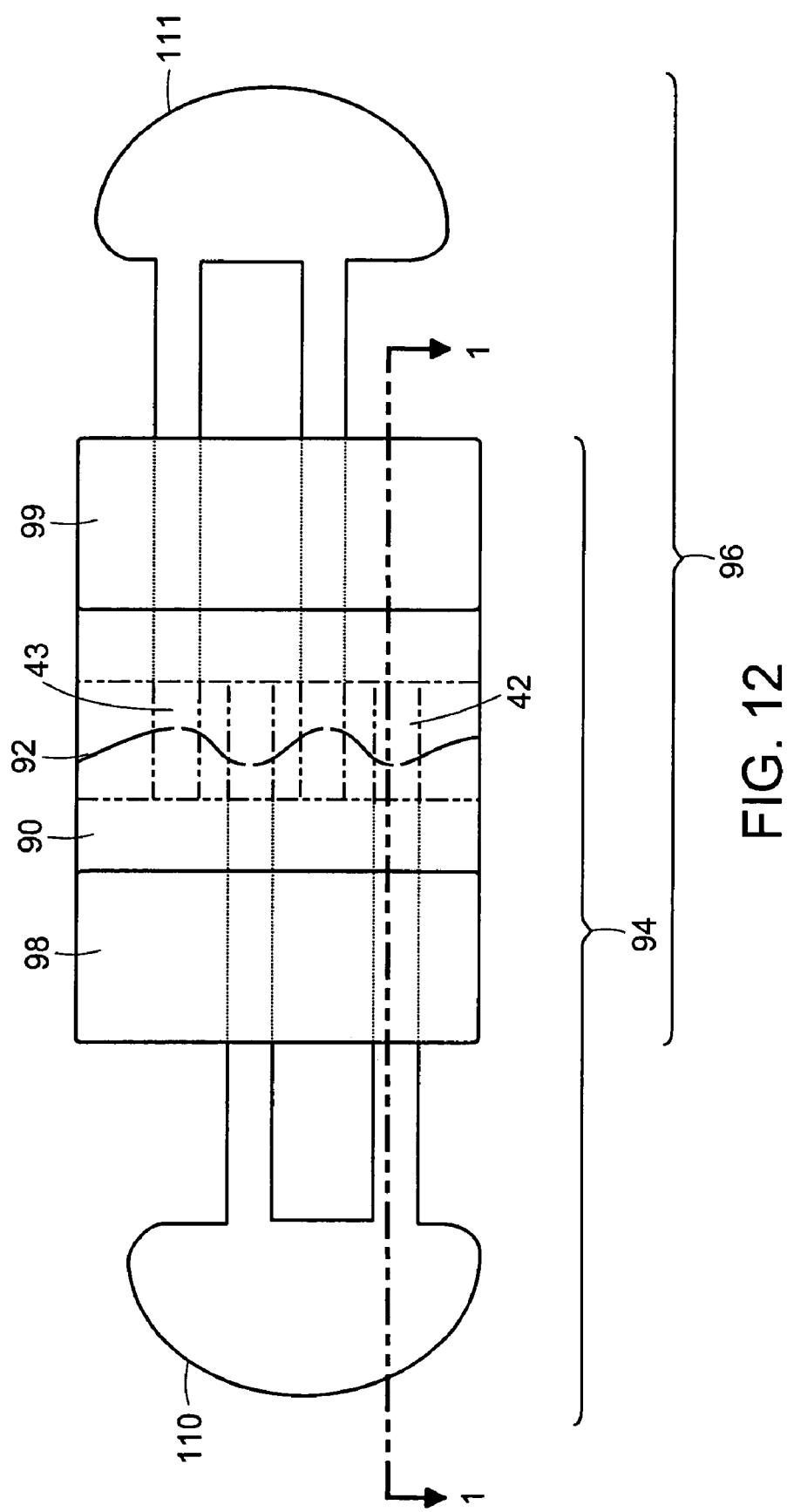
FIG. 12 is a bottom view of a wound closure device of the present invention including a strip of semi-rigid material applied across the mating zone and adhered to release liners protecting the adhesive-backed surfaces of a pair of anchoring elements.

Following the application of the strip of semi-rigid material, the final device cuts are, made to separate the devices from the selvage or, if only partially die cut, the web can be rolled for subsequent die cutting in conjunction with the final packaging equipment. FIG. 12 shows a completed device comprising a first interlaced element (94) and a second interlaced element (96). The completed device includes anchoring elements protected by release liners (98 and 99) and connecting elements and pulling elements protected by release liners (110 and 111) (partially in phantom). Portions of connecting members (42 and 43) generated through cross-mating zone cuts are not protected by a release liner and are shown in phantom beneath semi-rigid strip (90) with frangible line (92). Portions of release liners (98 and 99) which protect adhesive-backed surfaces of anchoring elements are also shown partially in phantom for this reason.

Figure 13:
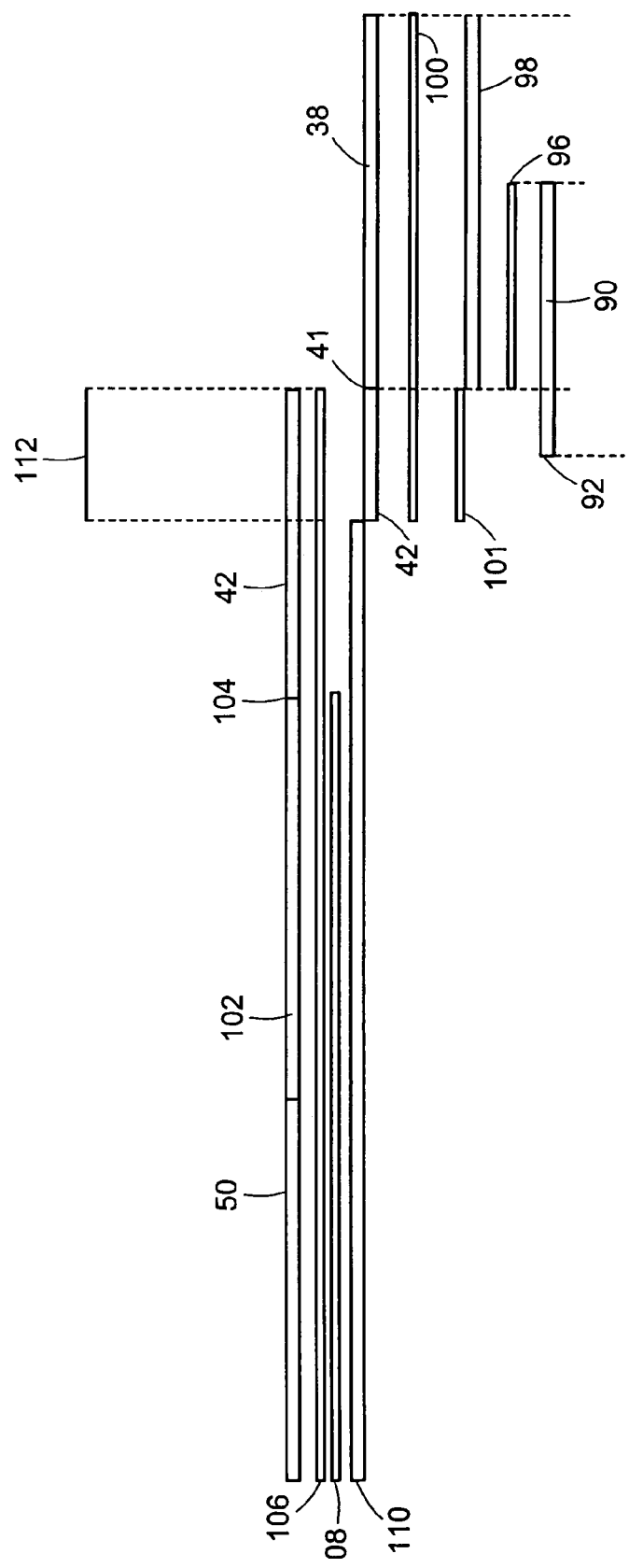
FIG. 13 is an exploded cross-sectional diagram taken along line 1-1 of FIG. 12.

A cross-section of the first interlaced element (94) of the device shown in FIG. 12, taken along line 1-1, is represented in FIG. 13. For purposes of this drawing, frangible line 92 has been broken and only one half of the portion remaining following processing of the strip of semi-rigid material is shown. Considering FIG. 13 in greater detail, one half of the strip of semi-rigid material (90) broken along frangible line (92) is connected by adhesive layer (96) to release liner (98). A second adhesive layer (100) joins release liner (98) to anchoring element (38). An adhesive-kill layer (101) is applied to the portion of adhesive layer (100) extending across the mating zone (112) on the lower surface of connecting element (42). Extending from the wound edge (41) of anchoring element (38) is a portion cut from bottom substrate layer (58 in FIG. 11) with cross-mating zone cuts (86 and 87 in FIG. 11). This portion represents one layer of connecting element (42) (connecting element 42 is comprised of an overlapping portion of the top and bottom substrate layer in the mating zone).

Referring now to the top portion of FIG. 13, pull tab (50), removable portion of connecting element (102) and connecting element (42) are portions of the first interlaced element (94) which are cut from bottom substrate layer (56 in FIG. 8). Perforation (104) defines the transition between the removable portion of connecting element (102) and the connecting element (42). Adhesive layer (106) was applied as a coating to the entire top surface of bottom substrate layer (56 in FIG. 8) at an early stage in processing. An adhesive kill layer (108) was applied as a coating to adhesive layer (106) in areas of the bottom substrate layer (56 in FIG. 8) to be cut to form pulling elements (50) and removable portions of connecting members (102). The purpose of the adhesive kill layer was to prevent the subsequently applied release liner (110) from adhering to pulling elements (50) and removable portions of connecting elements (44). Release liner (110) was applied to the portions of the top surface (60 in FIG. 8) of the bottom substrate layer (56 in FIG. 8) to the left and to the right of the mating zone. The only adhesive exposed to the release liner at these points of application are the single layer portions of connecting elements (42 in FIG. 13). Adhesive layer (106) is shown in FIG. 13 joining the overlapping portions of connecting member 42 contributed by the top substrate layer and bottom substrate layer. The bonded mating zone is shown as 112 in FIG. 13.

The invention claimed is:

1. A method for producing an interlaced device, the device comprising a first and a second interlaced element, each interlaced element comprising a mated first and second part, the first part having two termini and the second part having two termini, and a defined central void through which the other interlaced element passes, the method comprising:
   a) providing a first and a second substrate layer, the first and second substrate layers each comprising a top surface, a bottom surface and a mating zone, the first substrate layer to having a portion corresponding to a first part of a first interlaced element and a first part of a second interlaced element and the second substrate layer having a portion corresponding to a second part of a first interlaced element and a second part of a second interlaced element;
   b) introducing terminal end cuts in the first substrate layer for the first part of the first interlaced element and the first part of the second interlaced element;
   c) introducing cross-over point cuts in the first substrate layer for the first part of the first interlaced element first part of the second interlaced element;
   d) introducing terminal end cuts in the second substrate layer for the second part of the first interlaced element and the second part of the second interlaced element;
   e) introducing cross-over point cuts in the second substrate layer to define a cross-over point of the second part of the first interlaced element and a cross-over point of the second part of the second interlaced element;
   f) mating the top surface of the first substrate layer to the bottom surface of the second substrate layers by aligning the mating zones and interlaced element parts;
   g) bonding the top and bottom substrate layers along the mating zones; and
   h) completing, any cuts necessary to fully define the first and second interlaced elements.

2. The method of claim 1 wherein the first and second substrate layers are produced from a material selected from the group consisting of polymer, sheet metal, foil, textile and hide.

3. The method of claim 1 wherein the substrate layers are cut by a die cut process.

4. The method of claim 1 wherein the substrate layers are cut by a laser cutting device.

5. The method of claim 1 wherein the bonding of step g) is carried out using an adhesive.

6. The method of claim 1 wherein the bonding of step g) is carried out using an ultrasonic welding technique.

7. The method of claim 1 wherein step h) includes cutting away portions of the bonded mating zone which, in a preferred embodiment, do not directly link the first portion of a first interlaced element to the second portion of an interlaced element.

8. A method for producing an interlaced device, the device comprising at least two interlaced elements, each of the interlaced element comprising at least two parts with each part having at least two termini that are mated during production, and a defined central void through which at least one other interlaced element passes, the method comprising:
  a) providing at least a first and a second substrate layer, each substrate layer comprising a top surface, a bottom surface and a mating zone, the substrate layers to be processed to form at least four interlacing parts, each of the interlacing parts processed from a single substrate layer being mated with one part from another substrate layer to create an interlaced element;
  b) introducing terminal end cuts in each substrate layers for each interlacing part;
  c) introducing cross-over point cuts in each substrate layers to define cross-over points, with at least one cross-over point on each interlacing part;
  d) mating the substrate layers by aligning mating zones;
  e) bonding the substrate layers along the mating zones; and
  f) completing any cuts necessary to fully define the interlaced elements.

9. The method of claim 8 wherein the first and second substrate layers are produced from a material selected from the group consisting of polymer, sheet metal, foil, textile and hide.

10. The method of claim 8 wherein the substrate layers are cut by a die cut process.

11. The method of claim 8 wherein the substrate layers are cut by a laser cutting device.

12. The method of claim 8 wherein the bonding of step e) is carried out using an adhesive.

13. The method of claim 8 wherein the bonding of step e) is carried out using an ultrasonic welding technique.

14. The method of claim 8 wherein step f) includes cutting away portions of the bonded mating zone which do not directly link the first portion of a first interlaced element to the second portion of an interlaced element.

15. A method for manufacturing an interlaced two-component device useful for altering the spatial relationship between two surfaces, or two portions of a single surface, the two-component closure device comprising:
  a) a first component, the first component comprising:
    i) a first anchoring element for attachment to the surface of an article, the first anchoring element having an inner edge and an outer edge;
    ii) a plurality of first connecting elements extending from the inner edge of the first anchoring element, at least a portion of the plurality of first connecting elements having a two layer thickness;
    iii) a first pulling element having an outer edge, and an inner edge, the inner edge being joined to the plurality of first connecting elements;
  b) a second component, the second component comprising:
    i) a second anchoring element for attachment to the surface of an article, the second anchoring element having an inner edge and an outer edge;
    ii) a plurality of second connecting elements extending from the inner edge of the second anchoring element, at least a portion of the plurality of second connecting elements having a two layer thickness;
    iii) a second pulling element having an outer edge, and an inner edge, the inner edge being joined to the plurality of second connecting elements;
  c) means for attaching the first connecting elements to the second anchoring element and means for attaching the second connecting elements to the first anchoring element, the method for manufacturing comprising:
    i) providing a bottom substrate layer having a top surface, a bottom surface, a left edge, a right edge, and a mating zone and processing the bottom substrate layer according to the following steps:
      (1) cutting two parallel series of cut-outs, the first parallel cut-out series extending from the left edge of the mating zone toward the left edge of the bottom substrate layer, the second parallel cut-out series extending from the right edge of the mating zone toward the right edge of the bottom substrate layer, the portion of the bottom substrate layer remaining left of the mating zone between individual cut-outs in the first series of parallel cut-outs defining the connecting elements of a series of first components, the inner edge of the series of first pulling elements, and an edge to be further processed to define the inner edge of the first anchoring element, the portion of the bottom substrate layer remaining right of the mating zone between individual cut-outs in the second series of parallel cut-outs defining the connecting elements of a series of second components, the inner edge of the series of second pulling elements, and an edge to be further processed to define the inner edge of the second anchoring element;
    ii) providing a top substrate layer having a top surface, a bottom surface and a mating zone and processing the top substrate layer according to the following steps;
      (1) cutting a first and second series of slits at the two boundaries of the mating zone, the first and second series of slits forming the inner edges of the to-be-formed first and second anchoring elements;
      (2) cutting a third series of slits through the top substrate layer, the third series of slits defining the outer edge of the first anchoring element opposite its associated inner edge in the to-be-completed first anchoring element;
      (3) cutting a fourth series of slits through the top substrate layer, the fourth series of slits defining the outer edge of the second anchoring element opposite its associated inner edge in the to-be-completed second anchoring element;
    iii) aligning the bottom substrate layer and the top substrate layer in two dimensions and mating the top surface of the bottom substrate layer with the bottom surface of the top substrate layer;
    iv) bonding the mated top surface and bottom surface along the length of the mating zone;
    v) introducing a series of cross-mating zone cuts through both layers of the mated substrates thereby extending connecting elements from one side of the mating zone to the opposite side of the mating zone, each of the cross-mating zone cuts intersecting with a pre-existing cut on both sides of the mating zone;

vi) completing the formation of the first and second pulling tabs; and vii) introducing a series of cuts through the first and second substrate layers, the series of cuts intersecting with the second, third and fourth series of slits formed in step c)1), c)2) and c)3), thereby releasing individual, interlaced two-component closure devices.

16. The method of claim 15 wherein the first and second substrate layers are produced from a material selected from the group consisting of polymer, sheet metal, foil, textile and hide.

17. The method of claim 15 wherein the substrate layers are cut by a die cut process.

18. The method of claim 15 wherein the substrate layers are cut by a laser cutting device.

19. The method of claim 15 wherein the bonding of step c)iv) is carried out using an adhesive.

20. The method of claim 15 wherein the bonding of step c)iv) is carried out using an ultrasonic welding technique.

21. A method for manufacturing an interlaced wound closure device comprising two interlaced elements, each interlaced element being produced from two or more substrate layers, each interlaced element having a plurality of overlapping and bonded portions at which at least two substrate layers are joined to form an interlaced element, each interlaced element further comprising:

a) an adhesive-backed anchoring element having a substantially linear wound edge;

b) a plurality of connecting elements having removable and non-removable portions, the plurality of connecting elements extending from the wound edge in a first direction, at least a portion of the lower surface of the connecting elements being adhesive-backed; and c) a pulling element attached to the connecting members, the method of manufacturing comprising:

i) providing a bottom substrate layer having a top surface, a bottom surface, a left edge, a right edge and a center line bisecting a mating zone and processing the bottom substrate layer according to the following steps:

(1) applying to the top surface of the bottom substrate layer, a first adhesive layer suitable for securing a connecting element to an anchoring element when the device is in use;

(2) applying an adhesive-kill layer to the portions of the first, adhesive layer which will comprise the to-be-formed pulling elements, and removable portions of connecting elements;

(3) applying a first release liner along the left edges of the bottom substrate layer, the first release liner extending from the left edge of the bottom substrate layer toward the center line of the bottom substrate layer and terminating at the left edge of the mating zone;

(4) applying a second release liner along the right edge of the bottom substrate layer, the second release liner extending from the right edge of the bottom substrate layer toward the center line of the bottom substrate layer and terminating at a point near the center line which defines the right edge of the mating zone;

(5) applying a third release liner covering adhesive previously applied over the mating zone;

(6) cutting two parallel series of cut-outs through the bottom substrate layer and associated release liners, the first parallel cut-out series extending from the left edge of the mating zone toward the left edge of the bottom substrate layer, the second parallel cut-out series extending from the right edge of the mating zone toward the right edge of the bottom substrate layer, the portion of the bottom substrate layer remaining left of the mating zone between individual cut-outs in the first series of parallel cut-outs defining the connecting elements of a series of first interlaced elements, the portion of the bottom substrate layer remaining right of the mating zone between individual cut-outs in the second series of parallel cut-outs defining connecting elements of a series of second interlaced elements;

ii) providing a top substrate layer having a top surface, a bottom surface and a center line bisecting a mating zone and processing the top substrate layer according to the following steps;

(1) applying a second adhesive layer to the top surface of the top substrate layer, the second adhesive layer comprising an adhesive suitable for securing an anchoring element to the skin of an individual when the device is in use;

(2) applying an adhesive-kill layer to a portion of the second adhesive layer comprising the mating zone;

(3) applying a fourth release liner to the portion of the second adhesive layer exposed to the left side of the mating zone following the adhesive-kill step;

(4) optionally applying a first longitudinal crease in the fourth release liner, the first longitudinal crease being substantially parallel to the margin of the mating zone, the position of the first longitudinal crease in the X-dimension of the fourth release liner falling within the boundary of the to-be-formed second adhesive-backed anchoring element;

(5) applying a fifth release liner to the portion of the second adhesive layer exposed to the right side of the mating zone following the adhesive-kill step, (6) optionally applying a second longitudinal crease, the second longitudinal crease being applied to the fifth release liner, the second longitudinal crease being substantially parallel to the margin of the mating zone, the position of the second longitudinal crease in the X-dimension of the fifth release liner falling within the boundary of the to-be-formed first adhesive-backed anchoring element;

(7) applying a third adhesive layer and a protective release liner to the portion of the fourth release liner bounded in the X-dimension by the adhesive-killed portion, and the first longitudinal crease, if present, or by an imaginary line drawn to meet the positioning requirements of the first longitudinal crease;

(8) applying a fourth adhesive layer and a protective release liner to the portion of the fifth release liner bounded in the X-dimension by the adhesive-killed portion, and the second longitudinal crease, if present, or by an imaginary line drawn to meet the positioning requirements of the second longitudinal crease;
(9) cutting a first and second series of slits at the two boundaries of the mating zone, the first and second series of slits forming the wound edges of the to-be-formed first and second adhesive-backed anchoring elements;
(10) cutting a third series of slits through the fourth release liner and the attached top substrate layer, the third series of slits defining an edge of the first adhesive-backed anchoring element opposite its associated wound edge in the to-be-completed first adhesive-backed anchoring element;
(11) cutting a fourth series of slits through the fifth release liner and the attached top substrate layer, the fourth series of slits defining an edge of the second adhesive-backed anchoring element opposite its associated wound edge in the to-be-completed second adhesive-backed anchoring element;
iii) removing the third release liner from the top surface of the bottom substrate layer;
iv) aligning the top and bottom substrate layers in two dimensions and mating the top surface of the bottom substrate layer with the bottom surface of the top substrate layer using the adhesive layer exposed by the removal of the third release liner;
v) introducing cross-mating zone cuts to extend connecting elements, portions of which are pre-existing in the bottom substrate layer, across the mating zone, each cross-mating zone cut intersecting with a pre-existing cut in both the top and bottom substrate layers on both sides of the mating zone;
vi) removing the release liner from the third and fourth adhesive layers;
vii) applying to the adhesive layers exposed in the preceding step, a strip of semi-rigid material to be further processed to form a series of first and second members of a series of flip tab pairs, the left edge of the strip being aligned with the outer edge of the third adhesive layer, the right edge of the strip being aligned with the outer edge of the fourth adhesive, the strip being incompletely cut to form a frangible line in the area applied over the mating zone of the mated top and bottom substrate layers;
viii) completing the formation of the first and second pulling tabs by introducing any necessary cuts; and
ix) introducing a series of cuts through all layers of the mated assembly, the series of cuts intersecting with the second, third and fourth series of slits, thereby releasing individual, interlaced two-component wound closure devices.

22. An interlaced wound closure device comprising two separate and distinct interlaced elements, each interlaced element being produced from two or more substrate layers, each interlaced element having a plurality of overlapping and bonded portions at which the at least two substrate layers are joined to form an interlaced element, wherein the bonded portions have inner and outer perimeters and wherein the inner and outer perimeter of the bonded portions of the two or more substrate layers are substantially identical and substantially aligned with each other thereby forming the overlapped bonded portion, each interlaced element further comprising:
i) an adhesive-backed anchoring element having a substantially linear wound edge;
ii) a plurality of connecting elements extending from the wound edge in a first direction, at least a portion of the lower surface of the connecting elements being adhesive-backed; and
iii) a pulling element attached to the connecting elements.

23. The device of claim 22 wherein the connecting elements comprise removable and non-removable portions and the pulling element is attached to the removable portion.

24. The device of claim 23 wherein the removable and non-removable portions of the connecting elements are separated by a perforation in the connecting elements.

25. The device of claim 22 wherein the adhesive-backed portions of the device are protected by release liners.

26. The device of claim 22 wherein the overlapping and bonded portions of each interlaced element comprise portions of connecting elements.

27. The device of claim 26 wherein the portions of connecting elements comprise those portions which span the area over a laceration or incision, between two attached anchoring elements, in an applied device.

28. The device of claim 27 further comprising an applied strip preserving an as manufactured relationship of the two interlaced elements.

29. The device of claim 28 wherein the applied strip is produced from a semi-rigid polymer.

30. The device of claim 28 wherein the as-manufactured relationship of the two interlaced elements comprises parallel, spaced-apart relation between wound edges of the two interlaced elements.

31. The device of claim 30 wherein the applied strip produced from a semi-rigid polymer spans the spaced-apart portion between parallel wound edges and is adhered to portions of release liners protecting adhesive-backed surfaces of anchoring elements.

32. The device of claim 31 wherein the applied strip produced from a semi-rigid polymer is incompletely cut to form a frangible line.

33. A method for producing an interlaced device, the device comprising at least two interlaced elements, at least one of every two of the interlaced elements comprising at least two parts with each part having at least two termini ends that are mated during production, and a defined central void through which at least one other interlaced element passes, the method comprising:
a) providing at least a first and a second substrate layer, each substrate layer comprising a top surface, a bottom surface and a mating zone, the substrate layers to be processed to form at least two interlacing parts, each of the interlacing parts processed from a single substrate layer being mated with one part from another substrate layer to create an interlaced element;
b) introducing terminal end cuts in each substrate layers for each of its interlacing parts;
c) introducing cross-over point cuts in each substrate layer to define cross-over points for each interlacing parts;
d) mating the substrate layers by aligning mating zones;
e) bonding the substrate layers along the mating zones; and
f) completing any cuts necessary to fully define the interlaced elements.

34. The method of claim 33 wherein the first and second substrate layers are produced from a material selected from the group consisting of polymer, sheet metal, foil, textile and hide.

35. The method of claim 33 wherein the substrate layers are cut by a die cut process.

36. The method of claim 33 wherein the substrate layers are cut by a laser cutting device.

37. The method of claim 33 wherein the bonding of step g) is carried out using an adhesive.

38. The method of claim 33 wherein the bonding of step g) is carried out using an ultrasonic welding technique.

39. The method of claim 33 wherein step h) includes cutting away portions of the bonded mating zone which, in a preferred embodiment, do not directly link the first portion of a first interlaced element to the second portion of an interlaced element.

* * * * *